United States Patent [19]

Vidal

[11] Patent Number: 5,232,911
[45] Date of Patent: Aug. 3, 1993

[54] MIXTURE OF A NON-COVALENT HETERODIMER COMPLEX AND A BASIC AMPHIPHATIC PEPTIDE AS CYTOTOXIC AGENT

[75] Inventor: Juan C. Vidal, Boston, Mass.

[73] Assignee: Ventech Research Inc., Cambridge, Mass.

[21] Appl. No.: 734,534

[22] Filed: Jul. 23, 1991

Related U.S. Application Data

[63] Continuation-in-part of Ser. No. 460,508, Jan. 3, 1990, Pat. No. 5,164,196.

[51] Int. Cl.$^5$ .................... A61K 37/02; A61K 37/48; C07K 15/08
[52] U.S. Cl. .................... 514/12; 424/94.3; 424/542; 514/21; 530/300; 530/324; 530/350; 530/856
[58] Field of Search .............. 530/300, 324, 350, 856; 514/2, 12, 21; 435/197; 424/94.3, 94.6, 542

[56] References Cited

U.S. PATENT DOCUMENTS

| | | | |
|---|---|---|---|
| 4,731,439 | 3/1988 | Marquardt et al. | 530/324 |
| 4,774,318 | 9/1988 | Marquardt et al. | 530/324 |
| 5,053,492 | 10/1991 | Rael et al. | 530/856 |
| 5,164,196 | 11/1992 | Plata et al. | 424/542 |

OTHER PUBLICATIONS

Aird et al, "Rattlesnake Presynaptic Neurotoxins...", *Biochemistry*, vol. 24, 1985, pp. 7054–7058.
Boudnier et al, "Cloning and sequencing of cDNAs encoding the two subunits of Crotoxin", Nucleic Acids Research, 16(18), 1988, p. 9050.
Breithaupt et al, "Isolation and Characterization of Three Phospholipases...", *Biochim. Biophys. Acta.* vol. 403, 1975, pp. 355–369.
Chemical Abstracts 86:11908d (1977).
Narita et al, "The Amino Acid Sequence of Cardiotoxin From Formosan Cobra...", *Biochem. Biophys. Res. Comm.* 41(2) 1970, pp. 339–343.
Braganca, Patel & Bardinath, 1967, Biochem, Biophys. Acta 333–345.
Takechi, Sasaki & Hayashi, 1971, Naturwissenshaften, 58, 323.
Cotte, Eddenfeld, Yahr & Calvo Lairet, 1972, Toxicon, 10, pp. 157–163.

*Primary Examiner*—Jeffrey E. Russel
*Attorney, Agent, or Firm*—William R. Ritchie

[57] ABSTRACT

Novel cytotoxic agent useful against malignant tumors. It provides a stable composition of matter based on the cytotoxic activity of two synergistically acting toxins which sequence are herein described. The basic amphipathic peptide binds to the cell membrane causing perturbation of the lipid bilayer. The non-covalent heterodimer complex dissociates and the phospholiphase A$_2$ subunit (B) binds to the cell membrane. Subunit A acts as a chaperon preventing non-specific binding of the phospholipase A$_2$, it has no enzymatic activity. The basic amphipathic peptide increases the effect of the phospholipase A$_2$ subunit. Cell death is caused by the enzymatic hydrolysis of cell membrane phospholipids. Both the non-covalent heterodimer complex and the basic amphipathic peptide used were purified from the venoms of *Crotalus durissus terrificus* and *Naja naja atra*, respectively.

4 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 122
( B ) TYPE: AMINO ACID
( C ) STRANDEDNESS: NOT APPLICABLE
( D ) TOPOLOGY: LINEAR ( i i ) MOLECULE TYPE: PROTEIN ( v i ) ORIGINAL SOURCE:
( A ) ORGANISM: Crotalus durissus terrificus ( i x ) FEATURE:
( A ) NAME/KEY: PHOSPHOLIPASE A2 ACTIVE SITE
( B ) LOCATION: His 47, Asp 89
( C ) IDENTIFICATION METHOD: selective inactivation by alkylation of His 47 with 1, 4-dibromoacetophenone and similarity with other phospholipases A2.
( D ) OTHER INFORMATION: neurotoxicity, blockage of neuromuscular transmission at the pre-synaptic level. Binds to subunit A in a 1:1 stoichiometry and to acidic phospholipids. Less abundant isoforms contain Ser in position 1, Gln in position 33, Arg in position 37, Pro or Gly in position 65, and Arg in position 69. The position of the disulfide bonds are: Cys 26-Cys 115; Cys 28-Cys 44; Cys 43-Cys 95; Cys 49-Cys 122; Cys 50-Cys 86; Cys 57-Cys 81; Cys 75- Cys 88.

( x i ) SEQUENCE DESCRIPTION: SEQ ID NO:1:

| His | Leu | Leu | Gln | Phe | Asn | Lys | Met | Ile | Lys | Phe | Glu | Thr | Arg | Lys |
|---|---|---|---|---|---|---|---|---|---|---|---|---|---|---|
| 1 | | | | 5 | | | | | 10 | | | | | 15 |
| Asn | Ala | Ile | Pro | Phe | Tyr | Ala | Phe | Tyr | Gly | Cys | Tyr | Cys | Gly | Trp |
| | | | | 20 | | | | | 25 | | | | | 30 |
| Gly | Gly | Arg | Gly | Arg | Pro | Lys | Asp | Ala | Thr | Asp | Arg | Cys | Cys | Phe |
| | | | | 35 | | | | | 40 | | | | | 45 |
| Val | His | Asp | Cys | Cys | Tyr | Gly | Lys | Leu | Ala | Lys | Cys | Asn | Thr | Lys |
| | | | | 50 | | | | | 55 | | | | | 60 |
| Trp | Asp | Ile | Tyr | Arg | Tyr | Ser | Leu | Lys | Ser | Gly | Tyr | Ile | Thr | Cys |
| | | | | 65 | | | | | 70 | | | | | 75 |
| Gly | Lys | Gly | Thr | Trp | Cys | Glu | Glu | Gln | Ile | Cys | Glu | Cys | Asp | Arg |
| | | | | 80 | | | | | 85 | | | | | 90 |
| Val | Ala | Ala | Glu | Cys | Leu | Arg | Arg | Ser | Leu | Ser | Thr | Tyr | Lys | Tyr |
| | | | | 95 | | | | | 100 | | | | | 105 |
| Gly | Tyr | Met | Phe | Tyr | Pro | Asp | Ser | Arg | Cys | Arg | Gly | Pro | Ser | Glu |
| | | | | 110 | | | | | 115 | | | | | 120 |
| Thr | Cys | | | | | | | | | | | | | |

( 2 ) INFORMATION FOR SEQ ID NO:2:

( i ) SEQUENCE CHARACTERISTICS:

-continued (A) LENGTH: 38
(B) TYPE: AMINO ACID
(C) STRANDEDNESS: NOT APPLICABLE
(D) TOPOLOGY: LINEAR (ii) MOLECULE TYPE: PEPTIDE A (vi) ORIGINAL SOURCE:
(A) ORGANISM: Crotalus durissus terrificus (ix) FEATURE:
(D) OTHER INFORMATION: Formation of a 1:1
complex with subunit B (Seq ID NO:1)
Inhibition of phospholipase A2
activity, potentiation of
neurotoxicity. Peptide A (SEQ ID NO:2)
crosslinked with Peptide B (SEQ ID
NO:3) and Peptide C (SEQ ID NO:4)
constitute the Subunit A of crotoxin
complex.
The disulfide bonds which crosslink
Peptide A (SEQ ID NO:2) with Peptide B
(SEQ ID NO:3) and Peptide C (SEQ ID
NO:4) are: Cys 4 SEQ ID NO:2-Cys 7 of
SEQ ID NO:4; Cys 21 of SEQ ID NO:2-Cys
27 of SEQ ID NO:3; Cys 27 of SEQ ID
NO:2 -Cys 14 of SEQ ID NO:4; Cys 28 of
SEQ ID NO:2 - Cys 18 of SEQ ID NO:3;
Cys 35 of SEQ ID NO:2 - Cys 13 of SEQ
ID NO:3.
An intrapeptidic disulfide bond is
established between Cys 6 and Cys 22 of
SEQ ID NO:2

(xi) SEQUENCE DESCRIPTION: SEQ ID NO:2:

Ser Tyr Gly Cys Tyr Cys Gly Ala Gly Gly Gln Gly Trp Pro Gln
1               5                   10                  15

Asp Ala Ser Asp Arg Cys Cys Phe Phe His Asp Cys Cys Tyr Ala
                20                  25                  30

Lys Leu Thr Gly Cys Asn Pro Thr
                35

(2) INFORMATION FOR SEQ ID NO:3:

(i) SEQUENCE CHARACTERISTICS:
(A) LENGTH: 34
(B) TYPE: AMINO ACID
(C) STRANDEDNESS: NOT APPLICABLE
(D) TOPOLOGY: LINEAR (ii) MOLECULE TYPE: PEPTIDE B (vi) ORIGINAL SOURCE:
(A) ORGANISM: Crotalus durissus terrificus (ix) FEATURE:
(D) OTHER INFORMATION: Formation of a 1:1
complex with subunit B (SEQ ID NO:1)
Inhibition of phospholipase A2
activity, potentiation of
neurotoxicity. Peptide B
(SEQ ID NO:3) crosslinked with Peptide
A (SEQ ID NO:2) and Peptide C (SEQ ID
NO:4) constitute the subunit A of the
crotoxin complex.
The disulfide bonds which crosslink
Peptide B (SEQ ID NO:3) with Peptide A
(SEQ ID NO:2) are: Cys 21 of SEQ ID
NO:2- Cys 27 of SEQ ID NO:3; Cys 28 of
SEQ ID NO:2 - Cys 18 of SEQ ID NO:3;
Cys 35 of SEQ ID NO:2 - Cys 13 of SEQ
ID NO:3. An intrapeptidic disulfide
bond is established between Cys 7 and
Cys 20 of SEQ ID NO:3
The amino acid in position 1 (Xaa) of
SEQ ID NO:3 is pyroglutamic acid.

(xi) SEQUENCE DESCRIPTION: SEQ ID NO:3:

```
Xaa Glu Asp Gly Ile Val Cys Gly Glu Asp Asp Pro Cys Gly Thr
 1               5                  10                  15

Gln Ile Cys Gly Cys Asp Lys Ala Ala Ala Ile Cys Phe Arg Asn
                20                  25                  30

Ser Met Asp Thr
```

(2) INFORMATION FOR SEQ ID NO:4:

(i) SEQUENCE CHARACTERISTICS:
                (A) LENGTH: 14
                (B) TYPE: AMINO ACID
                (C) STRANDEDNESS: NOT APPLICABLE
                (D) TOPOLOGY: LINEAR (ii) MOLECULE TYPE: PEPTIDE C (vi) ORIGINAL SOURCE:
                (A) ORGANISM: Crotalus durissus terrificus (ix) FEATURE:
                (D) OTHER INFORMATION: Formation of a 1:1 complex with subunit B (Seq ID No. 1) Inhibition of phospholipase A2 activity, potentiation of neurotoxicity. Peptide C (SEQ ID NO: 4) crosslinked with Peptide A (SEQ ID NO:2) and Peptide B (SEQ ID NO:3) constitute the subunit A of the crotoxin complex. The disulfide bonds which crosslink Peptide C (SEQ ID NO:4) with Peptide A (SEQ ID NO: 2) are: Cys 7 of SEQ ID NO:4 - Cys 4 of SEQ ID NO:2; Cys 14 of SEQ ID NO: 4 - Cys 27 of SEQ ID NO:2 The amino acid in position 1 (Xaa) of SEQ ID NO:4 is pyroglutamic acid.

(xi) SEQUENCE DESCRIPTION: SEQ ID NO:4:

```
Xaa Phe Ser Pro Glu Asn Cys Gln Gly Glu Ser Gln Pro Cys
 1               5                  10
```

(2) INFORMATION FOR SEQ ID NO:5:

(i) SEQUENCE CHARACTERISTICS:
                (A) LENGTH: 61
                (B) TYPE: AMINO ACID
                (C) STRANDEDNESS: NOT APPLICABLE
                (D) TOPOLOGY: LINEAR (ii) MOLECULE TYPE: PEPTIDE (vi) ORIGINAL SOURCE:
                (A) ORGANISM: Naja naja atra (ix) FEATURE:
                (D) OTHER INFORMATION: cytotoxicity, depolarization of smooth, skeletal and cardiac muscles. Activation of phospholipase A2, inhibition of neurotoxicity. The positions of the disulfide bonds in SEQ ID NO 5 are: Cys 3 - Cys 22; Cys 15 - Cys 39; Cys 43 - Cys 54; Cys 55 - Cys 60.

(xi) SEQUENCE DESCRIPTION: SEQ ID NO:5:

```
Leu Lys Cys Asn Lys Leu Val Pro Pro Phe Trp Ala Lys Thr Cys
 1               5                  10                  15

Pro Glu Gly Lys Asn Leu Cys Tyr Lys Met Tyr Met Val Ser Thr
                20                  25                  30

Pro Thr Val Pro Val Lys Arg Gly Cys Ile Asp Val Cys Pro Lys
                35                  40                  45
```

-continued

```
Asn Ser Ala Leu Val Lys Tyr Val Cys Cys Asn Thr Asp Lys Cys
            50                      55                    60
Asn
```

MIXTURE OF A NON-COVALENT HETERODIMER COMPLEX AND A BASIC AMPHIPHATIC PEPTIDE AS CYTOTOXIC AGENT

This is a continuation-in-part of U.S. patent application Ser. No. 460,508, filed Jan. 3, 1990, now U.S. Pat. No. 5,164,196.

BACKGROUND OF THE INVENTION

1. Field of the Invention

The invention relates generally to compositions of matter for use in the treatment of malignant tumors.

2. Description of the Related Art

The analgesic effect of snake venoms proteins has been known since antiquity and several authors have pointed out the efficiency of the administration of crude cobra or rattlesnake venoms in the treatment of trigeminal neuralgias, tabetic and pain caused by tumors. In the cases of tumoral pains, the patients could be maintained without the administration of morphine in 70% of the cases. Obviously, at that time crude venoms were employed without even an adequate knowledge of the source. Sometimes the venoms from cobras captured in India or in South Africa were employed indistinctly. However, several reports mentioned besides the analgesic effect, an improvement in the condition of the patients.

Independently, the first cytotoxic component to be isolated and purified to homogeneity from a snake venom was a cytotoxin obtained by BRAGANCA et al. from *Naja naja naja* venom. Braganca, B. M., Patel, N. T., & Bardinath, P. G., 1967, Biochem., Biophys. Acta, 333–345. TAKECHI et al. isolated two cytotoxins from the same venom having a high cytotoxic activity on tumor cells. Takechi, M., Sasaki, T. & Hayashi, K., 1971, Naturwissenshaften, 58, 323. COTTE et al. showed the cytotoxic effects of Crotalus and Bothrops venoms on several cell lines. Cotte, C. A., Eddenfeld-Yahr, E. and Calvo Lairet A., 1972, Toxicon, 10, 157–163. However, the high concentrations required (100 μg/ml) and the complexity in composition led to the conclusion that the cytotoxic action was a reflection of their non-specific toxic effects. On the other hand, recently, U.S. Pat. No. 4,731,439 and U.S. Pat. No. 4,774,318, issued to Hans Marquardt et al., discloses high cytotoxic activity of polypeptides with low molecular weight (Growth Arresting Peptides, "GAP") isolated from the venom of *Crotalus atrox*.

SUMMARY OF THE INVENTION

It is an object of the invention to provide a cytotoxic agent that displays cytocidal action against a wide variety of human and murine tumors.

It is another object of the invention to provide a cytotoxic agent that exhibits a low toxicity against normal human cell line cultures.

It is still another object of the invention to provide a combination of cytotoxic agents which exhibit greater pharmacological efficacy together than each acting alone.

It is still a further object of the invention to provide a cytotoxic agent which does not interfere with the DNA structure or metabolism of normal cells.

It is still another object of the invention to provide a cytotoxic agent that can be administered intraperitoneally, intramuscularly, or subcutaneously.

The present invention provides novel cytotoxic agents comprising a non-covalent heterodimer complex and a basic amphipathic peptide. The combination of these agents enhances the cytotoxicity of the non-covalent heterodimer complex and reduces its toxicity. It may be used in the treatment of malignant tumors.

DETAILED DESCRIPTION OF THE INVENTION

Identification of differences between normal and tumor cells may result in the discovery of new anticancer agents which can counteract the uncontrolled proliferation of the disease-producing cells either by cytostatic or cytolytic mechanisms.

Applicant has isolated an antitumor enzymatic complex, which has phospholipase $A_2$ activity and displays cytotoxic (cytocidal) action against a wide variety of human and murine tumor cell lines cultures, while exhibiting a significantly lower cytotoxicity against cultures of normal human keratinocytes or 3T3-fibroblasts.

The cytotoxic (cytocidal) action of this complex is due to its binding to the plasma membrane of the target cells, followed by the structural membrane damage resulting from its enzymatic activity which eventually leads to cell lysis.

On this basis, the present invention differs radically from conventional chemotherapeutic agents, since it does not interfere with DNA structure or metabolism, and is not an antimetabolite or an enzyme inhibitor.

The present invention shows a highly significant activity in animal tumor models including rapidly proliferating murine leukemias or carcinogen induced tumor cell lines and slowly growing transplantable (xenograft) solid tumors.

This compound contains proteins, thus it can be administered intraperitoneally, intramuscularly, intravenously or subcutaneously but not orally, because it is destroyed in the digestive tract. It is rapidly metabolized, thus allowing to be administered two or three times a day. In addition, it is a poor antigen as indicated by the difficulty in raising antibodies, as shown by the very low antibody titres in the serum of the experimental animals.

The present invention is a mixture of a non-covalent heterodimer complex (CT) and a basic amphipathic peptide (CD). The complex can be dissociated in the following subunits:

(i) The subunit B (SEQ ID NO: 1) is a basic phospholipase $A_2$ with a mol. wt. 14500 and isoelectric point 9.7 formed by a single polypeptide chain of 122 amino acid residues crosslinked by seven disulfide bonds.

(ii) The subunit A (SEQ ID NO: 2; SEQ ID NO: 3; SEQ ID NO: 4) is an acidic polypeptide of mol. wt. 9500 and isoelectric point 3.5 which does not have any enzymatic activity.

The amino acid sequences for the subunits are as follows:

| | 1 | | | | | | | | | 10 | | | | | | | | | | 20 |
|---|---|---|---|---|---|---|---|---|---|---|---|---|---|---|---|---|---|---|---|---|
| Subunit B- | His | Leu | Leu | Gln | Phe | Asn | Lys | Met | Ile | Lys | Phe | Glu | Thr | Arg | Lys | Asn | Ala | Ile | Pro | Phe | Tyr |
| Subunit A- | | | | | | | | | | | | | | | | | | | | | |

-continued

|  |  |  |  |  | a |  | b | 30 |  |  |  | # |  |  |  | + |  |  | 40 |  |  |
|---|---|---|---|---|---|---|---|---|---|---|---|---|---|---|---|---|---|---|---|---|---|
| Subunit B- | Ala | Phe | Tyr | Gly | Cys | Tyr | Cys | Gly | Trp | Gly | Gly | # | Gly | Arg | Pro | + | Asp | Ala | Thr | Asp | Arg |
| Subunit A- |  | Ser | Tyr | Gly | Cys | Tyr | Cys | Gly | Ala | Gly | Gly | Gln | Gly | Trp | Pro | Gln | Asp | Ala | Ser | Asp | Arg |

|  | c | b |  |  |  | 50 | d | e |  |  |  |  |  |  | f |  | 60 |  |  |  |
|---|---|---|---|---|---|---|---|---|---|---|---|---|---|---|---|---|---|---|---|---|
| Subunit B- | Cys | Cys | Phe | Val | His | Asp | Cys | Cys | Tyr | Gly | Lys | Leu | Ala | Lys | Cys | Asn | Thr | Lys | Trp | Asp | Ile |
| Subunit A- | Cys | Cys | Phe | Phe | His | Asp | Cys | Cys | Tyr | Ala | Lys | Leu | Thr | Gly | Cys | Asn | Pro | Thr |  |  |  |

|  |  |  |  |  |  | + | 70 |  |  |  |  | g |  |  |  | 80 | F |  |  |  |
|---|---|---|---|---|---|---|---|---|---|---|---|---|---|---|---|---|---|---|---|---|
| Subunit B- | Tyr | Arg | Tyr | Ser | Leu | + | Ser | Gly | Tyr | Ile | Thr | Cys | Gly | Lys | Gly | Thr | Trp | Cys | Glu | Glu | Gln |
| Subunit A- |  |  |  |  |  | Xaa | Glu | Asp | Gly | Ile | Val | Cys | Gly | Glu | Asp | Asp | Pro | Cys | Gly | Thr | Gln |

|  |  | g | e | 90 |  |  |  |  |  | c |  |  |  |  | 100 |  |  |  |  |
|---|---|---|---|---|---|---|---|---|---|---|---|---|---|---|---|---|---|---|---|
| Subunit B- | Ile | Cys | Glu | Cys | Asp | Arg | Val | Ala | Ala | Glu | Cys | Leu | Arg | Arg | Ser | Leu | Ser | Thr | Tyr | Lys | Tyr |
| Subunit A- | Ile | Cys | Gly | Cys | Asp | Lys | Ala | Ala | Ala | Ile | Cys | Phe | Arg | Asn | Ser | Met | Asp | Thr |  |  |  |

|  |  |  |  | 110 |  |  |  |  | a |  |  |  |  | 120 | d |  |
|---|---|---|---|---|---|---|---|---|---|---|---|---|---|---|---|---|
| Subunit B- | Gly | Tyr | Met | Phe | Tyr | Pro | Asp | Ser | Arg | Cys | Arg | Gly | Pro | Ser | Glu | Thr | Cys |
| Subunit A- |  |  |  | Xaa | Phe | Ser | Pro | Glu | Asn | Cys | Gln | Gly | Glu | Ser | Gln | Pro | Cys | where:

# = Gln or Arg; + = Lys or Arg; Xaa = pyroglutamic acid, and letters over the Cys identify the positions of the half-cystine residue involved in a disulfide bond.

The following functional properties are relevant to the antitumor activity of the invention. The subunit B (SEQ ID NO: 1) is a phospholipase $A_2$ (EC 3.1.1.4.) which catalyzes the hydrolysis of the acyl ester bond in position 2 of the glycerol moiety of the 1,2-diacyl (phospholipids); 1-alkenyl-2-acyl (plasmalogens) or 1-alkyl-2-acyl(glyceryleters) sn-3-phosphoglycerides producing one molecule of free fatty acid and one molecule of 1-acyl(1-alkenyl or 1-alkyl) lysoderivative. The reaction is stereospecific and exhibits an absolute requirement for $Ca^{2+}$ ions as cofactor. It displays an extremely high reactivity towards the active site directed inhibitor p-bromophenacyl bromide and has an hydrophobic area close to the active site which binds nitroxide-labeled fatty acids (n=2, $Kd=1.5 \times 10^{-5}M$) which is thought to be involved in the tight binding of the subunit B (SEQ ID NO: 1) to phospholipid-water interfaces. Binding experiments to phospholipid aggregates show a strong preference for negatively charged surfaces as indicated by an apparent $K_D$ of $1-2 \times 10^{-3}M$ with zwitterionic PC or PC:PE vesicles, which falls to $5 \times 10^{-5}M$ for acidic phospholipids and to $<1 \times 10^{-6}M$ for phosphatidylinositol. The subunit B (SEQ ID NO: 1) binds to membranes like erythrocytes or electroplaques in a non-specific, non-saturable fashion.

The subunit A (SEQ ID NO: 2; SEQ ID NO: 3; SEQ ID NO: 4) has no enzymatic activity and does not bind to any phospholipid-water interface or biological membrane. When added in a 1:1 molar ratio to a solution of subunit B (SEQ ID NO: 1), but not to phospholipases $A_2$ from other sources, it forms a complex with a $K_D = 3 \times 10^{-9}M$ at pH 7.0 with mol. wt. 23800 and isoelectric point 4.7.

In the complex, the subunit A (SEQ ID NO: 2; SEQ ID NO: 3; SEQ ID NO: 4) reduces the accessibility of the hydrophobic area near the active site of the subunit B (SEQ ID NO: 1) as shown by its inability to react with p-bromophenacyl bromide or to bind nitroxide-labeled fatty acids. Also in the complex, the subunit B (SEQ ID NO: 1) becomes unable to interact with zwitterionic phospholipid-water interfaces; therefore its phospholipase $A_2$ activity is decreased to only 10–50% of that of the isolated subunit B (SEQ ID NO: 1). The inhibition of the unspecific binding of the subunit B (SEQ ID NO: 1) by complex formation with subunit A (SEQ ID NO: 2; SEQ ID NO: 3; SEQ ID NO: 4) also occurs with biological membranes like erythrocytes. With electroplaques, the non-specific, non-saturable binding of the isolated subunit B (SEQ ID NO: 1) is blocked by subunit A (SEQ ID NO: 2; SEQ ID NO: 3; SEQ ID NO: 4), remaining a saturable (specific) binding to a limited number of "high-affinity sites" existing on these postsynaptic membranes. Using doubly labeled complex, it was shown that only the subunit B (SEQ ID NO: 1) binds to membranes, while the subunit A (SEQ ID NO: 2; SEQ ID NO: 3; SEQ ID NO: 4) is released to the supernatant. This result indicates that the binding of the catalytically active subunit B (SEQ ID NO: 1) to a biological membrane requires the presence of some specific set of structural elements able to act as "high affinity sites" and thus capable to compete with subunit A (SEQ ID NO: 2; SEQ ID NO: 3; SEQ ID NO: 4) and to dissociate the complex. Furthermore, once the subunit B (SEQ ID NO: 1) is bound to either a phospholipid aggregate or a biological membrane, the addition of subunit A (SEQ ID NO: 2; SEQ ID NO: 3; SEQ ID NO: 4) cannot displace the enzyme to reform the complex.

The basic amphipathic peptide interacts with phospholipid-water interfaces or biological membranes perturbing the structure of the lipid bilayer and thus increasing the enzymatic activity of phospholipase $A_2$. Basic amphipathic peptides are found exclusively in Elapidae venoms. They constitute a large family of homolog peptides constituted by a single polypeptide chain of 61–62 amino acid residues crosslinked by 4 disulfide bonds between positions 3 and 22; 15 and 39; 44 and 53; 55 and 60, having several invariant amino acid residues around the half-cystines. In spite of the high degree of similarity with the postsynaptic neurotoxins, they are more basic (isoelectric point >9.3) and weakly toxic. The general structure and sequence of a typical cardiotoxin is presented below:

| 1 | | a | | | | | | | | 10 | | | | b | | | | | | 20 |
|---|---|---|---|---|---|---|---|---|---|---|---|---|---|---|---|---|---|---|---|---|
| Leu | Lys | Cys | Asn | Lys | Leu | Val | Pro | Pro | Phe | Trp | Ala | Lys | Thr | Cys | Pro | Glu | Gly | Lys | Asn | Leu |
| # | # | * | o | # | * | o | * | o | o | o | o | * | * | * | * | o | * | * | * | * |

| | | | | 25 | | | | | 30 | | | | | | | | | | 40 | |
|---|---|---|---|---|---|---|---|---|---|---|---|---|---|---|---|---|---|---|---|---|
| a | | | | | | | | | | | | | | | | | b | | | |
| Cys | Tyr | Lys | Met | Tyr | Met | Val | Ser | Thr | Pro | Thr | Val | Pro | Val | Lys | Arg | Gly | Cys | Ile | Asp | Val |
| * | * | # | * | o | # | # | o | o | o | o | o | * | * | * | * | * | * | * | # | * |

| | | 45 | | | | | 50 | | | | | | | | 60 | | | |
|---|---|---|---|---|---|---|---|---|---|---|---|---|---|---|---|---|---|---|
| c | | | | | | | | | | c | d | | | | d | | | |
| Cys | Pro | Lys | Asn | Ser | Ala | Leu | Val | Lys | Tyr | Val | Cys | Cys | Asn | Thr | Asp | Lys | Cys | Asn |
| * | * | * | o | * | o | * | # | * | * | # | * | * | # | * | # | o | * | * |

The letters over the Cys identify the positions of the half-cystine residues involved in a disulfide bond. (*) invariant residues; (#) highly frequent (>66% occurrence); (o) variable residues (33–66% occurrence). By analogy with that of postsynaptic neurotoxins, the structure of cardiotoxins is represented by three loops, linked in the central part of the molecule by the disulfide bonds. Cardiotoxicity appears to be related to the amino acid residues present in loops 2 and 3. They are able to form complexes with acidic phospholipids; have a weak intrinsic phospholipase $A_2$ activity, but are able to increase the enzymatic activity of other phospholipases $A_2$ on either artificial substrates or biological membranes. Among the effects induced by these peptides, it has been described as cytolysis, depolarization of the muscular membrane and inhibition of the $Na^+$-$K^+$ ATP-ase. In spite of their weak lethal potency ($LD_{50}$ i.v., mice=2.0–4.4 mg/Kg, s.c.=40–60 mg/Kg), when administered in high doses they may produce depolarization of myocardial cells, of other striated as well as of smooth muscles probably by affecting some structures associated with the modulation of $Ca^{2+}$ fluxes.

The cytotoxic action on tumor cells involves the binding of the basic amphipathic peptide and the dissociation of the complex and the interaction of the catalytically active subunit B (SEQ ID NO: 1) to the surface followed by the enzymatic hydrolysis of the membrane phospholipids.

The following facts support this interpretation:
(i) The cytotoxic (cytocidal) activity of the complex on murine erythroleukemia cells is extremely rapid: in the presence of 10 μg/ml, 68% killing occurred after 1 hr incubation, and after 12.5 hr the killing was 100%. With the human tumor cell line Hs 578T, the exposure to 10 μg/ml killed 90% of the cells in 6 hours. Since morphological changes were accompanied by the release of cytoplasmic enzymes (LDH) to the supernatant, it can be concluded that the cytocidal action is due to damage of the plasma membrane of the target cells. This effect is increased at least three-fold by the basic amphipathic peptide.
(ii) The synergistic effect of the basic amphipathic peptide and the subunit B (SEQ ID NO: 1) of the complex is responsible for the cytocidal activity. The addition of isolated subunit B (SEQ ID NO: 1) was cytotoxic on both, normal and tumor cells. The basic amphipathic peptide displays cytotoxic activity which is more drastic on several tumor cell lines than in normal cell lines. No cytotoxic effects were observed by incubation of cells with concentrations up to 20 μg/ml of isolated subunit A (SEQ ID NO: 2; SEQ ID NO: 3; SEQ ID NO: 4).
(iii) Phospholipase $A_2$ of the subunit B (SEQ ID NO: 1) is essential for its cytocidal action. Incubation of murine erythroleukemia cells with a modified complex (i.e. with the N3 on the imidazole ring of His 47 of the subunit B (SEQ ID NO: 1) selectively alkylated with 1,4'-dibromoacetophenone) lacking phospholipase $A_2$ activity did not decrease the number of cells even after four days exposure to concentrations up to 40 μg/ml.
(iv) However, the recognition of the surface of the target cells is independent of the phospholipase $A_2$ activity. Murine erythroleukemia cells incubated with the above mentioned (inactive) complex exhibited significantly altered surface properties (e.g., extensive attachment to the plastic substratum of the growing flask, decreased size) and an increased sensitivity to the cytocidal action of phospholipases $A_2$ (like unmodified complex or the enzymes from *Naja naja atra* and *Crotalus atrox* venoms).
(v) In contrast to the effect of isolated subunit B (SEQ ID NO: 1), which affects in a similar degree normal and tumor cells, the complex displays a certain degree of selectivity. For example, upon exposure to 10 μg/ml, 100% of murine erythroleukemia cells were killed after 12.5 hr and 85% of Hs 578T were killed after 6 hr, while 20% 3T3 fibroblasts and 60% normal human keratinocytes were still viable after four days incubation. The difference in sensitivity seems not to be attributable to the growing state of the tumor cells since the complex was cytocidal to murine erythroleukemia cells under culture conditions which either stimulated or suppressed cell division. Furthermore, the non-growing cells appeared to be more sensitive to the complex ($IC_{50}$~2.0 μg/ml) than the growing cells ($IC_{50}$~4.0 μg/ml).
(vi) Although exploitable differences between the properties of plasma membranes of normal and malignant cells are hard to define, in order to explain why some tumor cells are more sensitive to the cytotoxic action of this complex, the following possibilities should be considered:
(a) These cells, besides being altered by the binding of the basic amphipathic peptide, may establish and maintain in their neighborhood a set of physicochemical conditions which promote the dissociation of the complex and the subsequent binding of the catalytically active subunit B (SEQ ID NO: 1) to the membrane.
(b) The membrane of these tumor cells may contain a larger number (density) of structural elements which may function like acceptors or "high affinity sites" for the subunit B (SEQ ID NO: 1) and are able to compete efficiently with the subunit A (SEQ ID NO: 2; SEQ ID NO: 3; SEQ ID NO: 4) in the complex.

(c) In addition, these tumor cells may have a reduced capacity to compensate for the structural perturbation of the membrane produced by the binding of the basic amphipathic peptide and that of the subunit B (SEQ ID NO: 1) as well as for the increase in the local concentration of the products of phospholipid hydrolysis.

EXAMPLES

IN VITRO

In vitro results show that although CT does not evidence significant selectivity on the different tumor cell lines, the response is different according the cell line employed. Thus, colon cancer lines appear to be the most resistant to crotoxin. Among leukemia lines tested, the sensitivity seems to be similar in three of the lines, while one of them (MOLT-4) appears to be as resistant as the colon cancer lines. Six lines of CNS-cancer (except SNB-19 and SF-539), six lines of melanoma (except SK-MEL-2 and LOX IMVI) and the two lines of small cell lung cancer appears to be more sensitive in terms of the $IC_{50}$. With the non-small cell lung cancer lines tested, the sensitivities vary with $IC_{50}$ values from 3.2 ug/ml [EKVX, HOP-18, HOP-62] to 14.9 ug/ml [NCI-H 322, A 549]. Intermediate sensitivities were found with the lines of ovarian and renal cancer.

The addition of CD from Naja naja atra venom in a molar ratio crotoxin:cardiotoxin 1:3 resulted in various degrees of increased cytotoxicity to most of the tumor cell lines tested, and the results of [tumor cell line(s)]; TGI ($\sim IC_{50}$) in ug/ml and (n-fold decrease with respect to crotoxin) are presented below.

(a) Leukemias
[HL-60 (TB)] = 0.72 (7-fold)
[K-562, CCRF-CEM] = 1.97 +/−0.2 (2.7-fold)
[MOLY-4] = 5.73 (6.1-fold)
(b) Non-Small Cell Lung Cancer
[EKVX, HOP-18, HOP-62, NCl-H 460, NCl-H 522] =
0.069 +/−0.16 (5- to 7-fold)
[HOP-92] = 2.36 (2-fold).
[NCl-H 23, NCl-H 322, A 549] = 4.2 +/−0.2 (3-fold)
(c) Small Cell Lung Cancer
[DMS 114] = 2.92 (1.6-fold)
[DMS 273] = 0.55 (9-fold)
(d) Colon Cancer
[COLO 205, DLD-1, HCT-15, HCT-116, KM 12, HCC-2998, SW 620] = 4.75 +/−1.2 (6-fold)
[HT-29, KM 20 L2] = 19.4 (3-fold)
(e) CNS Cancer
[SF-539, SF-268, SNB-75, XF 498, U 251] = 0.48 +/−0.08
(10 fold)
[SNB-78] = 1.1 (4-fold)
[SF-295] = 2.09 (2-fold)
[SNB-19] = 8.4 (no increase)
(f) Melanoma
[MALME-3M, SK-Mel-28, SK-MEL-5, UACC-257, UACC-62] = 0.51 +/−0.02 (10-fold)
[LOX IMVI, M-19-MEL] = 1.74 +/−0.12 (4-fold)
(g) Ovarian Cancer
[IGROV 1] = 1.92 (3-fold)
[OVCAR-8, OVCAR-3, OVCAR-4] = 2.6 +/−0.5 (2.5-fold)
[OVCAR-5, SK-OV-3] = 4.78 +/−0.09 (8-fold)
(h) Renal Cancer
[CAKl-1, RXF-393 L]= 0.8 +/−0.1 (5- to 7-fold)
[SN 12C, UO-31] = 3.5 +/−0.2 (1.6 fold)
[A 498] = 5.38 (1.5-fold).

As shown by the experimental results, the mixture of CT-CD results in increased cytotoxicity to several of the tumor cell lines employed in this study. The mixture exhibited a more intense cytotoxic action particularly against five cell lines of CNS cancer and five cell lines of melanoma, where the $IC_{50}$ is 10-fold lower than that determined with crotoxin alone.

Regarding the other lines of CNS cancer, SNB-19 which is the less sensitive cell line to the mixture CT-CD was also the less sensitive to CT. The line SF-539 (the less sensitive to crotoxin) becomes one of the most sensitive to crotoxin-cardiotoxin On the other hand, the line SNB-78, reasonably sensitive to crotoxin is one o the less sensitive to the mixture, with a decrease in the $IC_{50}$ of only 2-fold.

A similar behavior is observed with some lines of melanoma. The lines SK-MEL-2 and LOX IMVI which were the less sensitive to crotoxin are the less sensitive to crotoxin-cardiotoxin, while the line M-19-MEL, reasonably sensitive to crotoxin is one of the less sensitive to the mixture with a decrease in the $IC_{50}$ of 3-fold only.

In the group of leukemias, the decrease in $IC_{50}$ is variable with the different lines from 7-fold (HL-60 (TB)) to 3-fold (K-562, CCRF-CEM) and the less sensitive to crotoxin (MOLT-4) is also the less sensitive to crotoxin-cardiotoxin, in spite of a decrease in $IC_{50}$ of 6-fold.

In the group of non-small cell lung cancer, there is a moderate decrease in $IC_{50}$ from 5- to 8-fold compared to that of crotoxin in five cell lines. The lines NCl-H 23 and HOP-92 which were reasonably sensitive to crotoxin show a decrease in $IC_{50}$ of only 1.2- and 2-fold, respectively with crotoxin-cardiotoxin. Finally, the lines NCl-H 322 and A 549, which were the less sensitive to crotoxin are the less sensitive to crotoxin-cardiotoxin, in spite of the 4-fold decrease in the $IC_{50}$ value.

In the group of small cell lung cancer, the line DMS 114 displays almost similar sensitivity to crotoxin and to crotoxin-cardiotoxin, while the line DMS 273 (which had a sensitivity to crotoxin similar to that of DMS 114) shows a decrease in $IC_{50}$ of nearly 9-fold with crotoxin-cardiotoxin.

In the group of colon cancer, there is a decrease in the $IC_{50}$ of 6-fold compared to that of crotoxin alone in seven cell lines. This is particularly clear with the line HCC 2998 which is one of the less sensitive to crotoxin and exhibits a decrease in $IC_{50}$ of near 10-fold with crotoxin cardiotoxin. The lines HT-29 and KM 20L2, the less sensitive to crotoxin are also the less sensitive to crotoxin-cardiotoxin with a decrease in $IC_{50}$ of only 2.5-fold.

In the group of ovarian cancer, there is a small decrease in $IC_{50}$ from 1.5- to 2.5-fold in five cell lines, and a decrease of 8-fold with the line OVCAR-5, compared to the values obtained with crotoxin alone.

In the group of renal cancer, there is a significant decrease in the $IC_{50}$ value from 5- to 7-fold with the lines CAKl-1 and RXF-393 L and a small decrease of 1.5 - to 1.6-fold with the lines SN 12C, UO-31 and A 498.

IN VIVO

Murine erythroleukemia

Murine erythroleukemia cells (clone DS-19) suspended in Hanks balanced salt solution at a density of $7 \times 10^6$ cells/ml were injected subcutaneously (0.1 ml or approximately $7 \times 10^5$ cells) close to the right rear limb into 30 DBA/2 mice (male, 20–23 g).(day=0). At day 4 animals were randomized in three groups: control, treated with low dose regime and treated with high dose regime and the treatment was started. CT was administered i.p. in 0.15M NaCl in volumes of 0.05-0.07 ml in the lower part of the left side of the abdomen.

The treatment was administered daily, with a progressive increase in dosage over the entire period of the experiment (30 days). For animals with low dose regime, the treatment started with 0.0195 mg/kg on day 4 and was increased progressively up to 0.78 mg/kg.

For animals with high dose regime, the treatment started with 0.065 mg/kg on day 4 and was increased progressively up to 1.56 mg/kg. The controls were injected with similar volumes of sterile 0.15M NaCl.

Body weights were recorded daily and tumor volumes were measured at intervals of 2-3 days by means of a Vernier caliper. Upon death (or sacrifice) of the animals, the tumors were dissected, weighed and fixed together with organs for histologic examination.

Fifty percent of the control mice died at day 23 and all the remaining at day 30. The tumors evolved rapidly and reached 8-12 g, accounting for about 60% of the total weight of the mice. They were composed by highly anaplastic cells with abundant mitotic cells (170 per 10 HPF), infiltrating muscle and bone. The spleen showed multiple areas of tumor infiltration in sheets.

In mice treated with low dose regime, only four developed tumor masses of 8-10 g. Microscopically, the tumor appeared surrounded by connective tissue without infiltrating muscle. The mitosis were fewer (about 59 per 10 HPF), and the spleen showed scattered, small clusters of tumor cells at high magnification. The percentage reduction of tumor volumes were 54% (day 8); 68% (day 11); 53% (day 15) and 48% (days 18-23).

In only three of the mice treated with high dose regime the tumors were larger than 1.0 g and in all the animals there was a reduction between 75-82% compared to controls during the full period of observation. One exhibited a full remission; it was kept for an additional 60 days without treatment and then sacrificed. No histologic evidence of tumor was found.

MET-A (Methycholantrene induced mammary tumor)

MET-A cells ($1 \times 10^5$) were injected i.p. into 24 B6 mice and on day 1 they were randomized and separated into two groups, controls and treated.

CT in 0.15M NaCl was administered at a single, high dose regime during the full period of the experiment (30 days).

The treatment started on day 1 with the administration of 0.16 mg/kg via i.p. and 0.16 mg/kg via i.m. from day 1 to day 9 and 0.32 mg/kg via i.m. from day 10 to day 30. The control group received injections of similar volumes of 0.15M NaCl. Body weights were recorded each three days.

Fifty percent of the control mice died at day 18 and all the remaining control mice died at day 25. The necropsies showed the evolution of a typical ascites tumor.

Only one of the treated mice died on day 7 although the cause of death is not clear. The treatment of the remaining 11 mice was suspended on day 30 and they were followed for additional 45 days. Since no evidence of tumor evolution was observed, they were sacrificed. The pathology report was negative. Therefore, treatment with crotoxin at high dosage level determined the full remission of the tumor. No evidences of toxicity were observed in treated mice.

MX-1 Human Mammary Carcinoma Xenograft

MX-1 Human mammary carcinoma was grown in athymic female nude mice (Swiss Nu/Nu). It was harvested and cut into fragments of approximately 30.0 mg. The fragments were implanted into 24 Swiss Nu/Nu female mice subcutaneously into the axillary region through a puncture in the inguinal region on day=0. When the tumors grew approximately 100 mg (day=10) the animals were randomized into groups of 12 and treatment was started.

CT was administered in 0.15M NaCl by intramuscular injection daily during the full period of the experiment (34 days) with a progressively increasing dosage starting with 0.04 mg/kg and ending with 0.8 mg/kg. The control animals were injected i.m. with similar volumes of sterile 0.15M NaCl. Body weights were recorded daily during the treatment. Tumor volumes were determined twice a week by Vernier caliper. Once measured (length$\times$width), tumor volume was calculated by the formula (length$\times$width$^2\times$0.5). Tumor growth inhibition was estimated by determining the change in tumor volume during the course of the experiment with respect to initial volume for each group and subsequently by calculating the ratio treated/control. The tumors in treated animals exhibited a range of responses from mild effects to full regressions (3), and reduced tumor growth by 80 percent relative to tumors in control mice. Two deaths occurred during the course of the experiment, both apparently unrelated to the treatment.

B16 Melanoma

B16 melanoma cells ($\sim 2\times 10^6$ cells per animal) were injected i.p. into 12 males and 12 females B6D2F$_1$ mice. At day 2 the animals were randomized and treatment with CT-CD was started on day 3.

CT-CD in phosphate buffered saline was administered daily via i.m. during 30 days with a progressively increasing dosage starting at 0.36 mg/kg and ending at 5.4 mg/kg. Controls were injected with phosphate buffered saline and body weights were recorded daily.

The mean survival time of control mice (males and females) was 19.5 days and all of them died on day 26. The necropsies showed large tumor masses (about 6-8 g) occupying the peritoneal cavity from the perineum up to the diaphragm. Microscopically, the tumor consisted of spindle shaped fibroblasts containing melanine, with large areas (25-75%) of necrosis and 20-35 mitosis per 10 HPF. Twenty five percent of the animals exhibited small metastatic foci in the hepatic portal tract, but no extrahepatic metastases were detectable.

The mean survival time of treated mice was 25.5 days, and all of them died on day 39 (Increase Life Span=125%). The necropsies showed tumor masses (1.6-3.5 g) occupying the lower third of the peritoneal cavity. Microscopically, the same type of tumor cells were found, again with necrotic regions comprising 35-60% of the area examined, and 4-10 mitosis per 10 HPF. No evidence of metastasis were found in liver or in other organs.

In a second experiment, a lower number of B16 Melanoma cells ($2.4\times 10^5$ cells) were injected i.p. into 30 B6D2F$_1$ mice. At day 2 after injection the animals were randomized and treatment with CT-CD was started on day 3. CT-CD in phosphate buffered saline was administered via i.m. during 30 days with a progressively increasing dosage starting at 0.09 mg/kg and ending at 2.34 mg/kg. The mean survival time for control mice was 29.5 days and for treated mice was 47.7 days, with an increase in life span of 162%.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. A pharmaceutical composition for the treatment of malignant tumors comprising a mixture of a non-covalent heterodimer complex isolated from the venom of *Crotalus durissus terrificus* and a basic amphipathic peptide isolated from the venom of *Naja naja atra*.

2. A pharmaceutical composition according to claim 1, wherein said heterodimer further comprises a subunit A (SEQ ID NO:2; SEQ ID NO:3; SEQ ID NO: 4) and a subunit B(SEQ ID NO:1) of the following sequence:

3. A pharmaceutical composition according to claim 1, wherein said peptide further comprises the following sequence (SEQ ID NO:5):

```
 1                                       10                                    20
              a                                         b
Leu  Lys  Cys  Asn  Lys  Leu  Val  Pro  Pro  Phe  Trp  Ala  Lys  Thr  Cys  Pro  Glu  Gly  Lys  Asn  Leu
 #    #    *    o    #    *    o    *    o    o    o    o    *    *    *    *    o    *    *    *
              25                       30                                              40
 a                                                                                b
Cys  Tyr  Lys  Met  Tyr  Met  Val  Ser  Thr  Pro  Thr  Val  Pro  Val  Lys  Arg  Gly  Cys  Ile  Asp  Val
 *    *    #    *    o    #    #    o    o    o    o    o    *    *    *    *    *    *    *    #    *
              45                       50                            c    d                60  d
 c
Cys  Pro  Lys  Asn  Ser  Ala  Leu  Val  Lys  Tyr  Val  Cys  Cys  Asn  Thr  Asp  Lys  Cys  Asn
 *    *    *    o    *    o    *    #    *    *    #    *    *    #    *    #    o    *    *
``` where:
the letters over the Cys identify the positions of the half-cystine residues involved in a disulfide bond; (*) invariant residues; (#) highly frequent (>66% occurrence); (o) variable residues (33–66% occurrence).

4. A method of treating malignant tumors comprising administering an efficacious dose of a mixture of a crotoxin complex purified from venom of *Crotalus durissus terrificus* and a cardiotoxin purified from venom of *Naja naja atra*.

```
              1                                              10                                           20
Subunit B-   His  Leu  Leu  Gln  Phe  Asn  Lys  Met  Ile  Lys  Phe  Glu  Thr  Arg  Lys  Asn  Ala  Ile  Pro  Phe  Tyr
Subunit A-
                                           30                                            40
                              a    b
Subunit B-   Ala  Phe  Tyr  Gly  Cys  Tyr  Cys  Gly  Trp  Gly  Gly   #   Gly  Arg  Pro   +   Asp  Ala  Thr  Asp  Arg
Subunit A-        Ser  Tyr  Gly  Cys  Tyr  Cys  Gly  Ala  Gly  Gly  Gln  Gly  Trp  Pro  Gln  Asp  Ala  Ser  Asp  Arg
                                                        50                                            60
              c    b                          d    e                              f
Subunit B-   Cys  Cys  Phe  Val  His  Asp  Cys  Cys  Tyr  Gly  Lys  Leu  Ala  Lys  Cys  Asn  Thr  Lys  Trp  Asp  Ile
Subunit A-   Cys  Cys  Phe  Phe  His  Asp  Cys  Cys  Tyr  Ala  Lys  Leu  Thr  Gly  Cys  Asn  Pro  Thr
                                           70                                         g   80      F
Subunit B-   Tyr  Arg  Tyr  Ser  Leu   +   Ser  Gly  Tyr  Ile  Thr  Cys  Gly  Lys  Gly  Thr  Trp  Cys  Glu  Glu  Gln
Subunit A-                              Xaa  Glu  Asp  Gly  Ile  Val  Cys  Gly  Glu  Asp  Asp  Pro  Cys  Gly  Thr  Gln
                                  90                                            100
                   g         e
Subunit B-   Ile  Cys  Glu  Cys  Asp  Arg  Val  Ala  Ala  Glu  Cys  Leu  Arg  Arg  Ser  Leu  Ser  Thr  Tyr  Lys  Tyr
Subunit A-   Ile  Cys  Gly  Cys  Asp  Lys  Ala  Ala  Ala  Ile  Cys  Phe  Arg  Asn  Ser  Met  Asp  Thr
                              110                                                    120                     d
                                                                                                        a
Subunit B-   Gly  Tyr  Met  Phe  Tyr  Pro  Asp  Ser  Arg  Cys  Arg  Gly  Pro  Ser  Glu  Thr  Cys
Subunit A-                  Xaa  Phe  Ser  Pro  Glu  Asn  Cys  Gln  Gly  Glu  Ser  Gln  Pro  Cys
``` where:
\# = Gln or Arg; + = Lys or Arg; Xaa = pyroglutamic acid, and letters over the Cys identify the positions of the half-cystine residue involved in a disulfide bond.